(12) United States Patent
Koetter et al.

(10) Patent No.: US 7,081,102 B1
(45) Date of Patent: Jul. 25, 2006

(54) HINGED DORSAL CARPAL TUNNEL BRACE

(75) Inventors: Eric J. Koetter, Floyds Knobs, IN (US); Scott T. Morton, New Albany, IN (US)

(73) Assignee: Active Ankle Systems, Inc., Louisville, KY (US)

( * ) Notice: Subject to any disclaimer, the term of this patent is extended or adjusted under 35 U.S.C. 154(b) by 0 days.

(21) Appl. No.: 11/068,154

(22) Filed: Feb. 28, 2005

(51) Int. Cl.
*A61F 5/00* (2006.01)
(52) U.S. Cl. .................... 602/21; 20/16; 2/16; 128/878
(58) Field of Classification Search .................. 602/16, 602/20, 21, 64; 2/16; 128/878, 879, 892; 482/44, 45, 46
See application file for complete search history.

(56) References Cited

U.S. PATENT DOCUMENTS

| | | | |
|---|---|---|---|
| 2,312,523 A | 3/1943 | Corbett | |
| 3,707,963 A | 1/1973 | Keropian | |
| 4,677,971 A | 7/1987 | Lindemann | |
| 4,782,825 A | 11/1988 | Lonardo | |
| 4,840,168 A | 6/1989 | Lonardo | |
| 4,941,460 A | 7/1990 | Working | |
| 4,977,890 A | 12/1990 | Mann | |
| 5,067,479 A | 11/1991 | Saringer et al. | |
| 5,158,298 A | 10/1992 | Goins | |
| 5,163,678 A | 11/1992 | Rogers | |
| 5,205,812 A | 4/1993 | Wasserman | |
| 5,254,078 A | 10/1993 | Carter et al. | |
| 5,358,471 A | 10/1994 | Klotz | |
| 5,415,623 A | 5/1995 | Cherubini | |
| 5,466,192 A | 11/1995 | Castolo et al. | |
| 5,520,625 A | 5/1996 | Malewicz | |
| D371,845 S | 7/1996 | Varn | |
| 5,637,078 A | 6/1997 | Varn | |
| 5,653,680 A | 8/1997 | Cruz | |
| 5,746,707 A | 5/1998 | Eck | |
| 5,766,142 A | 6/1998 | Hess | |
| 5,778,449 A | 7/1998 | Oetting et al. | |
| D404,818 S | 1/1999 | Cruz | |
| 6,540,710 B1 | 4/2003 | Cruz | |
| 6,716,185 B1 | 4/2004 | Rieger | |
| 6,773,410 B1 | 8/2004 | Varn | |
| 6,827,653 B1 * | 12/2004 | Be ............................... | 473/62 |
| 2002/0035342 A1 | 3/2002 | Williams | |
| 2004/0019306 A1 * | 1/2004 | Brewer ........................ | 602/21 |
| 2004/0138597 A1 | 7/2004 | Varn | |

* cited by examiner

*Primary Examiner*—Henry Bennett
*Assistant Examiner*—Amanda Wieker
(74) *Attorney, Agent, or Firm*—James E. Cole; Middleton Reutlinger (57) ABSTRACT

A hinged dorsal carpal tunnel brace comprises a first substantially arcuate splint portion for fastening to a dorsal side of a patient's forearm. The first splint portion includes at least one strap for fastening the first arcuate splint portion to the patient's forearm. A second splint portion attaches to a dorsal side of the patient's hand and includes at least one strap for fastening to the patient's hand. A hinge pivotally connects the first splint portion to the second splint portion and allows pivotal motion through a preselected arcuate distance in radial and ulnar directions.

22 Claims, 12 Drawing Sheets

HINGED DORSAL CARPAL TUNNEL BRACE

CROSS REFERENCES TO RELATED APPLICATIONS

None.

STATEMENT REGARDING FEDERALLY SPONSORED RESEARCH OR DEVELOPMENT

None.

REFERENCE TO SEQUENTIAL LISTINGS, ETC.

None.

INVENTOR(S)

Eric J. Koetter, 5511 Copper Creek, Floyds Knobs, Ind. 47119 USA;

Scott T. Morton, 423 Woodrow Avenue, New Albany, Ind. 47150 USA.

BACKGROUND

1. Field of the Invention

The present invention provides a Hinged Dorsal Carpal Tunnel Brace. More specifically, the present invention provides a dorsal carpal tunnel brace having a hinge and allowing increased mobility and utility of a patient utilizing the brace.

2. Description of the Related Art

Carpal Tunnel Syndrome (CTS) is a disorder caused by compression of a median nerve in the wrist that causes numbness or prickling in the hand. Left untreated, carpal tunnel syndrome can cause extreme pain, reduced hand dexterity, and, in rare cases, paralysis. Carpal tunnel syndrome is the most commonly reported repetitive stress injury. Carpal tunnel syndrome results from repetitive and forceful movements that can swell these tendons in the carpal tunnel, pinching the median nerve. Repetitive wrist movements that cause the wrist to bend at an awkward angle can also place pressure on the median nerve. Common repetitive activities that cause carpal tunnel syndrome include frequent or prolonged use of vibrating power tools or tools that require a strong hand grip, such as pitchforks or shovels, gripping the steering wheel of automobiles or other machinery, and typing or playing musical instruments.

The median nerve travels from the forearm into the hand through a carpal tunnel in the wrist. The bottom and sides of this tunnel are formed by wrist bones and the top of the tunnel is covered by a strong band of connective ligament tissue. The median nerve and nine tendons that move the fingers pass through the carpal tunnel. These tendons may enlarge and swell under some circumstances. If the swelling is sufficient it may cause the median nerve to be pressed up against this strong ligament which may result in numbness, tingling in the hand, clumsiness or pain described above. Alternatively, distortion of the carpal tunnel over an extended period of time may cause compression, irritation, or inflammation of the median nerve causing extreme discomfort to the patient resulting in long-term loss of mobility of the wrist.

Carpal tunnel syndrome can be treated by decreasing repetitive hand and wrist use, splinting the wrist to keep it from bending at an awkward angle, treating any medical conditions known to contribute to the problem, or anti-inflammatory drugs. If these methods do not relieve symptoms or if the syndrome is severe enough to cause progressive hand weakness and loss of feeling, surgery is usually recommended.

Since most patients dislike surgery and pharmaceutical treatments are relatively expensive, immobilization through splinting is typically chosen as the first option for treatment. Various prior art orthotic braces utilize rigid one piece designs to immobilize a patients hand. These devices severely limit everyday tasks that many people take for granted. Moreover, orthotic braces or splints are often worn during daytime hours while patients may be in a work environment. One deficiency of typical one-piece unitary brace designs is that these braces do not allow radial and ulnar motion that is, pivoting of the hand about a substantially vertical axis because doctors want to limit extension and flexion movement of the patient. Therefore one piece unitary braces severely limit patients' everyday tasks. Even further, most prior art one piece brace designs are volar positioned braces which means the braces extend along the lower surface of the arm rather than the upper surface of the arm. As a result, a portion of these braces typically engages the patients palm inhibiting use of the palm, which further limits everyday function and tasks.

Given the foregoing, it will be appreciated that a carpal tunnel brace is necessary which is dorsally positioned during use and allows radial and ulnar motion of the users hand to provide a least restrictive device to everyday functions and tasks.

SUMMARY OF THE INVENTION

A hinged dorsal carpal tunnel brace comprises a first substantially arcuate splint portion for fastening to a dorsal side of a patient's forearm. The first splint portion includes at least one strap for fastening the first arcuate splint portion to the patient's forearm. A second splint portion attaches to a dorsal side of the patient's hand and includes at least one strap for fastening to the patient's hand. A hinge pivotally connects the first splint portion to the second splint portion and allows pivotal motion through a preselected arcuate distance in radial and ulnar directions. Alternatively stated, the hinge design inhibits motion about a horizontal axis or in extension and flexion directions.

According to an alternative embodiment, a hinged dorsal carpal tunnel brace comprises a first splint portion having a thickened portion, a hinge area within the thickened portion, the thickened portion having a stop wall limiting rotation within the hinge area. A second splint portion pivotally connects the first splint portion within the hinge area. The first and second splint portions each comprise at least one strap for retaining the brace on a patient.

DETAILED DESCRIPTION

Referring now in detail to the drawings wherein, like numerals indicate like elements throughout the several views, there are shown in FIGS. 1–9 various aspects of a hinged dorsal carpal tunnel brace. The device functions to treat patients with carpal tunnel syndrome by inhibiting flexion and extension while allowing some limited motion in radial and ulnar directions.

Figure 1:
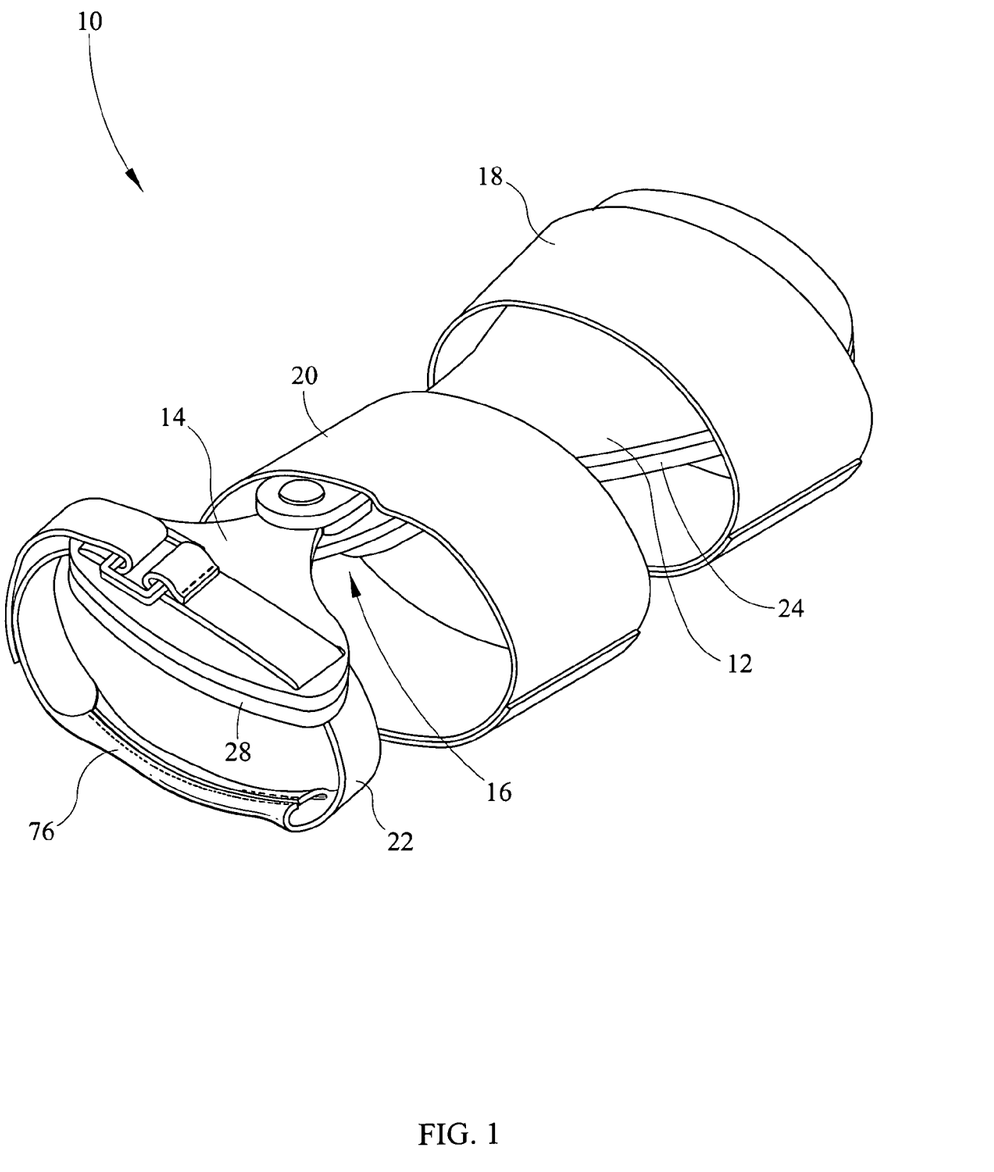
FIG. 1 is a perspective view of an exemplary hinged dorsal carpal tunnel brace of the present invention.

Referring specifically to FIG. 1, a perspective view of the hinged dorsal carpal tunnel brace 10 is depicted. The orthotic brace is disposed on a user's affected limb and extends from the dorsal forearm surface to the patient's dorsal hand surface. The hinged dorsal splint 10 is defined by a rigid first upper splint portion 12 and a rigid second lower splint portion 14. For purpose of this description the term "upper splint portion" refers to the splint portion toward the patient's arm and the term "lower splint portion" refers to the splint portion at the patient's hand. The first splint portion 12 is connected to the second splint portion 14 by a hinge 16 allowing radial and ulnar pivoting of the rigid second portion 14 when the splint 10 is worn by a patient. Further such arrangement inhibits pivoting about a horizontal axis, also known as flexion and extension. The hinged dorsal splint 10 is attached to the patient's arm by a plurality of straps. Specifically, the hinged dorsal splint 10 includes an upper arm strap 18 and a lower arm strap 20 which are connected to the rigid first splint portion 12 by a fastening device, adhesive, or the like. The upper arm strap 18 and the lower arm strap 20 may comprise hook and loop fastening material which extends around the rigid first splint portion 12 forming a loop and which may be extended around a patient's arm to allow a patient to wear the splint 10. The rigid second portion 14 further comprises a hand strap or finger loop 22 through which a user may place their fingers and which binds the second splint portion to the dorsal side of a patient's affected hand. The rigid first splint portion 12 further comprises an padding 24 along a lower surface of the first splint 12. The second splint portion 14 also comprises a padding 28 which is disposed on a lower surface of the second splint portion 14. The upper padding 24 and a lower padding 28 each engage the dorsal side of a patient's hand and arm when the dorsal splint 10 is being used in order to provide comfort to the patient during use. The pads 24,28 may be permanently attached or removably attached to the splint portions 12,14.

Figure 2:
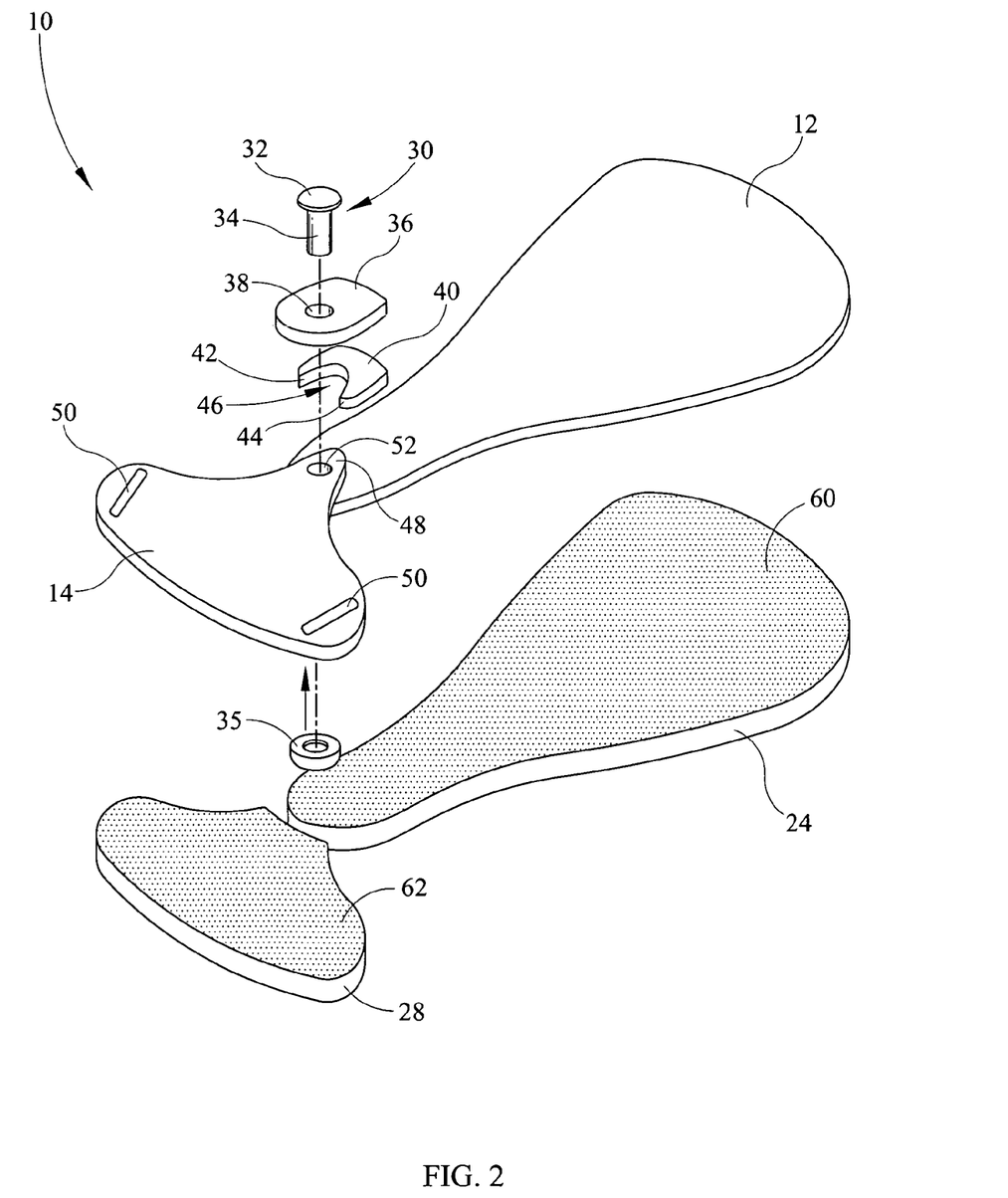
FIG. 2 is an exploded perspective view of the brace of FIG. 1.
Figure 9:
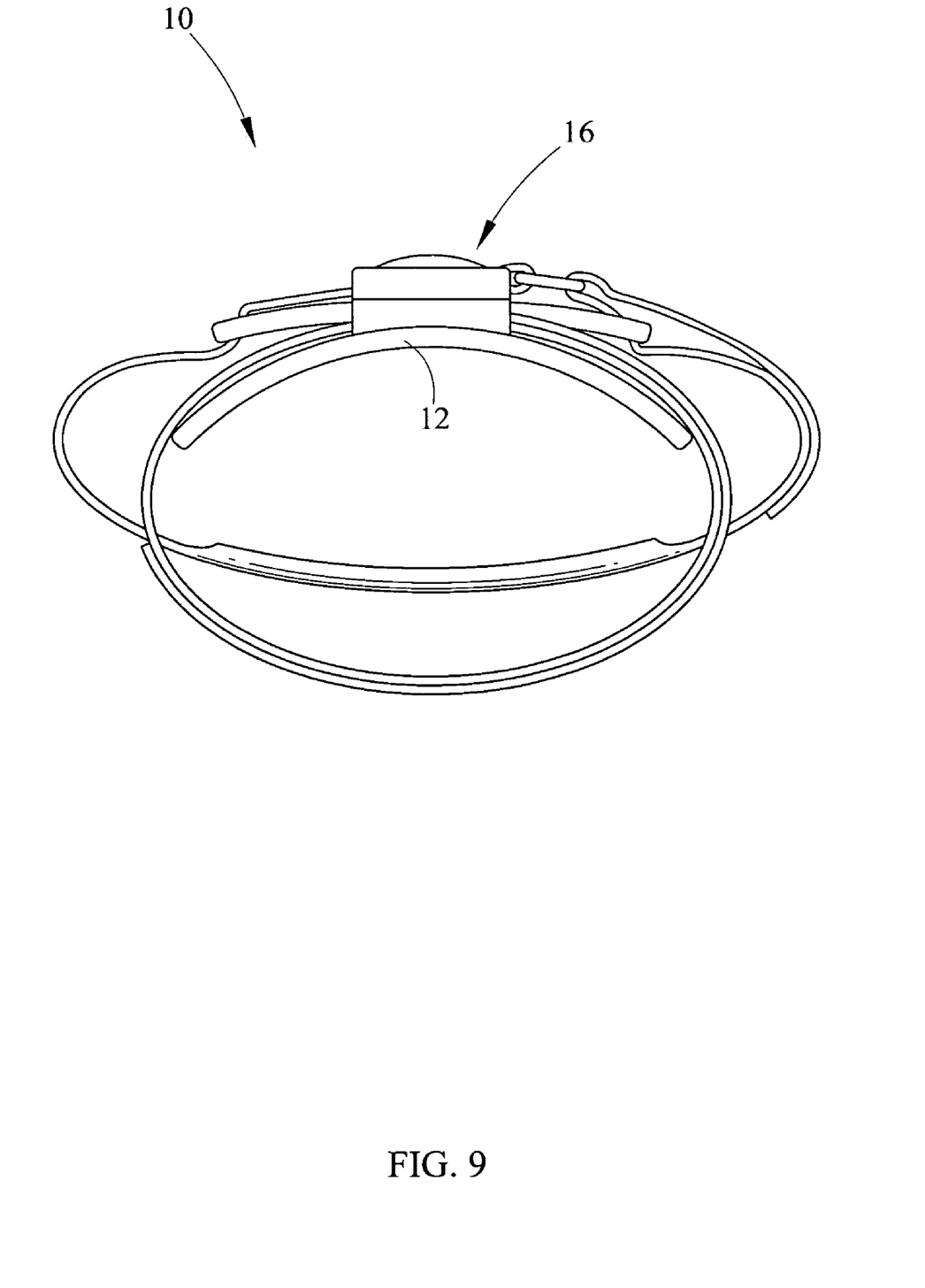
FIG. 9 is a top view of the brace with the straps in a fully extended position.

Referring now to FIG. 2, an exploded perspective view of the hinged carpal tunnel splint 10 is depicted with the straps 18, 20 and 22 removed. The first splint portion 12 and second splint portion 14 may be formed of a polymeric material which is preferably heat formable so that the splint portions 12, 14 may be heated and formed to a user's forearm and hand providing an improved ergonomic fit. Further, by heating the first and second splint portions 12, 14 the angle defined between the first and second splint portions 12, 14 may be altered to position the patient's wrist at an angle which is comfortable to the user while allowing healing of the tendons pressing on the median nerve. As shown in FIG. 9, the rigid first splint portion 12 and the rigid second splint portion 14 are arcuate in cross-section providing a better fit along the dorsal surface of the patient's forearm. In addition by heating the first and second splint portions 12,14 the device 10 is made to conform to an individual's arm. Referring back to FIG. 2, the exemplary first splint portion 12 comprises three sides and has an elongated slightly triangular shape with curvilinear sides. Various alternative shapes may be utilized which allow placement of the device on the dorsal surface of the patient's forearm. The uppermost region of the splint portion 12, toward the elbow, is the widest so that the arcuate shape of the first portion 12 extends along the dorsal area of the patient's arm and partially along the sides of the arm to stabilize the dorsal splint 10. At the lower portion of the first splint portion 12, toward the hand, the splint narrows and the hinge 16 connects the first splint portion 12 to the second splint portion 14. The first splint portion 12 has rounded corners to make the first splint portion 12 ergonomically preferable. The rigid first splint portion 12 further comprises a pin aperture (not shown) around the lowermost portion of the splint 12 in order to receive a pin 30 and provide the hinged motion relative to the second splint portion 14.

The rigid second splint portion 14 is also comprised of three sides wherein an uppermost portion is narrow and comprises a pin aperture 52 for receiving the pin 30 and providing the hinged motion relative to the first splint portion 12. The second splint 14 is positioned on an upper surface of the first splint 12 and the pin 30 extends through both splints 12,14. At the lower and wider portion of the second splint 14 are strap apertures 50 through which the hand strap 22 extends to form a loop through which a patient may position an affected hand. As previously indicated the hinge 16 comprises a pin 30 extending through the first and second splint portions 12, 14. The pin 30 comprises an upper head 32 and a shaft 34 which is cylindrical in shape and extends downwardly through the first and second splint portions 12, 14. The upper head 32 has a diameter that is larger than the aligned pin apertures 52 of the first and second splint portions 12, 14. Alternatively, various other hinge designs may be utilized which provide for a single degree of freedom, may be manufactured at a low cost, and do not change the dorsal positioning or rotational characteristics described herein.

Disposed on the dorsal surface of the first splint portion 12 is a rotation limiter or rotation limiting spacer 40. The spacer 40 is substantially U-shaped having opposed arms 42, 44. The arms 42, 44 define a recess 46 wherein a lobe 48 is disposed and may rotate through a pre-selected arcuate distance. The lobe 48 is disposed at the upper end of the second splint portion 14 and works along with the rotation limiting spacer 40 to only allow radial and ulnar movement of a patient's hand through a pre-selected arcuate distance. In other words, the rotation limiting spacer 40 in combination with the lobe 48 act as a stop device allowing limited rotation of the second splint 14 relative to the first splint 12 through a preselected arcuate distance. This movement allows a user to perform most tasks and functions without being severely limited by the carpal tunnel splint 10. The rotation limiting spacer 40 has a thickness which is substantially equal to or greater than the second splint portion 14 so that the lobe 48 engages the recess 46 and so that an upper washer 36 may extend across the rotation limiting spacer 40 and the upper surface of the second splint portion 14. The upper washer 36 may be comprised of various shapes and includes a pin aperture 38 through which pin 30 extends before extending through the second splint portion 14 and the first splint portion 12. The pin aperture 38 has a diameter which is slightly greater than the outer diameter of the shaft 34 thus allowing rotation of the upper washer 36 and first splint portion 12 relative to the second splint portion 14. Further, it is within the scope of the present specification that the spacer 40 and upper washer 36 may be combined into a single part partially defining the hinge 16, or that an alternative hinge 16 design be utilized having a single degree of freedom, or that the rotation limiter 40 be integrally formed with the first splint 12. Further the lobe 48 and rotation limiter 40 may be utilized on opposite splint portions.

The upper washer 36 of the exemplary embodiment is adhered to the rotation limiting spacer 40 which is adhered to the first splint portion 12. This arrangement locks the lobe 48 in position between the opposed arms 42, 44 of the rotation limiting spacer 40. This arrangement is utilized since the second splint portion 14 is positioned on top of the first splint portion 12. However, it is also well within the scope of the present specification that the first splint portion 12 may be disposed above the second splint portion 14 wherein the rotation limiting spacer 40 and washer 36 may be disposed on a lower surface of the first splint portion 12. An even further alternative, which is within the scope of the present specification, comprises a lobe 48 disposed on the first splint portion 12 and limiting spacer 40 and washer 36 being disposed on the second splint portion 14.

Beneath the upper and lower splint portion 12, 14 are the corresponding upper and lower splint pads 24, 28. The upper splint 24 pad may be formed of foam or other padded material and further may comprise a facecloth on the lower surface of the splint pad 24 which is disposed against the patient's skin. The upper surface of the pad 24 may include a hook and loop fastening material 60 which engages an opposed hook and loop fastener on the lowermost surface of the splint portion 12. This arrangement allows for removal of the pad 24 during heating of the rigid splint 12 and for cleaning of the facecloth. Alternatively, the pad 24 may be adhesively affixed to the splint portion 12. The second splint portion 14 also comprises a splint pad 28 which, like the upper splint pad 24, may be formed of foam or other padded material and may include a facecloth on a lower surface to engage the patient's skin. Further, the splint pad 28 may be fastened to the second splint 14 by hook and loop fasteners as previously described. Alternatively, the splint pad 28 may be adhered by adhesive to the second splint portion 14. The hinge 16 (FIG. 1) further includes a lower head 35 which engages the lower shaft 34 of pin 30 to lock the hinge 16 in place and inhibits disconnection of the second splint portion 14 from the first splint portion 12.

Figure 3:
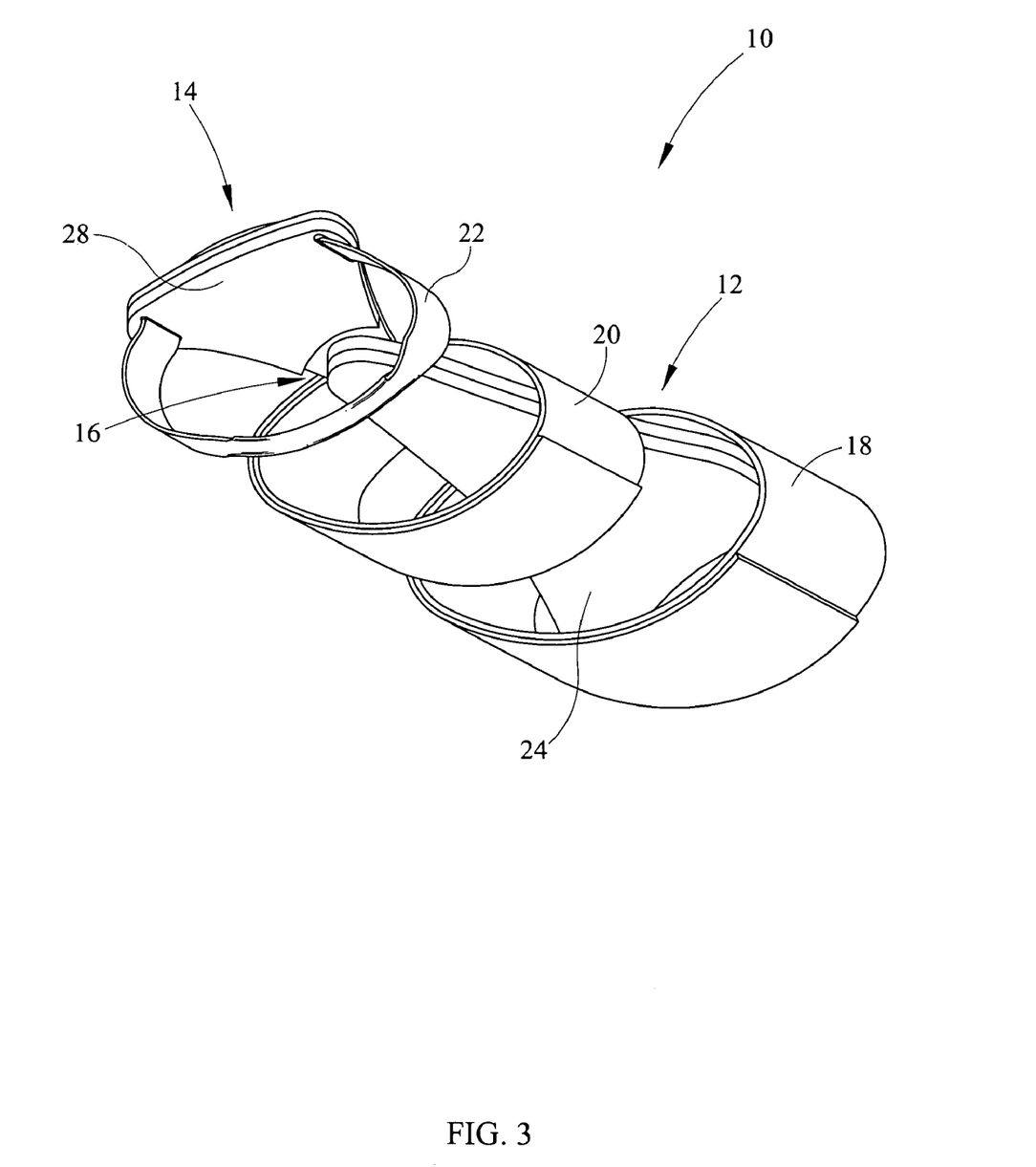
FIG. 3 is an upward perspective view of brace of FIG. 1.

Referring now to FIG. 3, a lower perspective view of the hinged carpal tunnel splint 10 is depicted. The straps 18, 20, and 22 are depicted depending from the first and second splint portions 12, 14. Further, the upper splint portion pad 24 is depicted extending over the hinge 16 so that a patient's wrist is not pinched by the hinge 16 above. Further, the lower splint portion pad 28 has a radial cut to receive the lowermost portion of the upper splint pad 24 allowing rotation while inhibiting interference between pads 24, 28.

Figure 4:
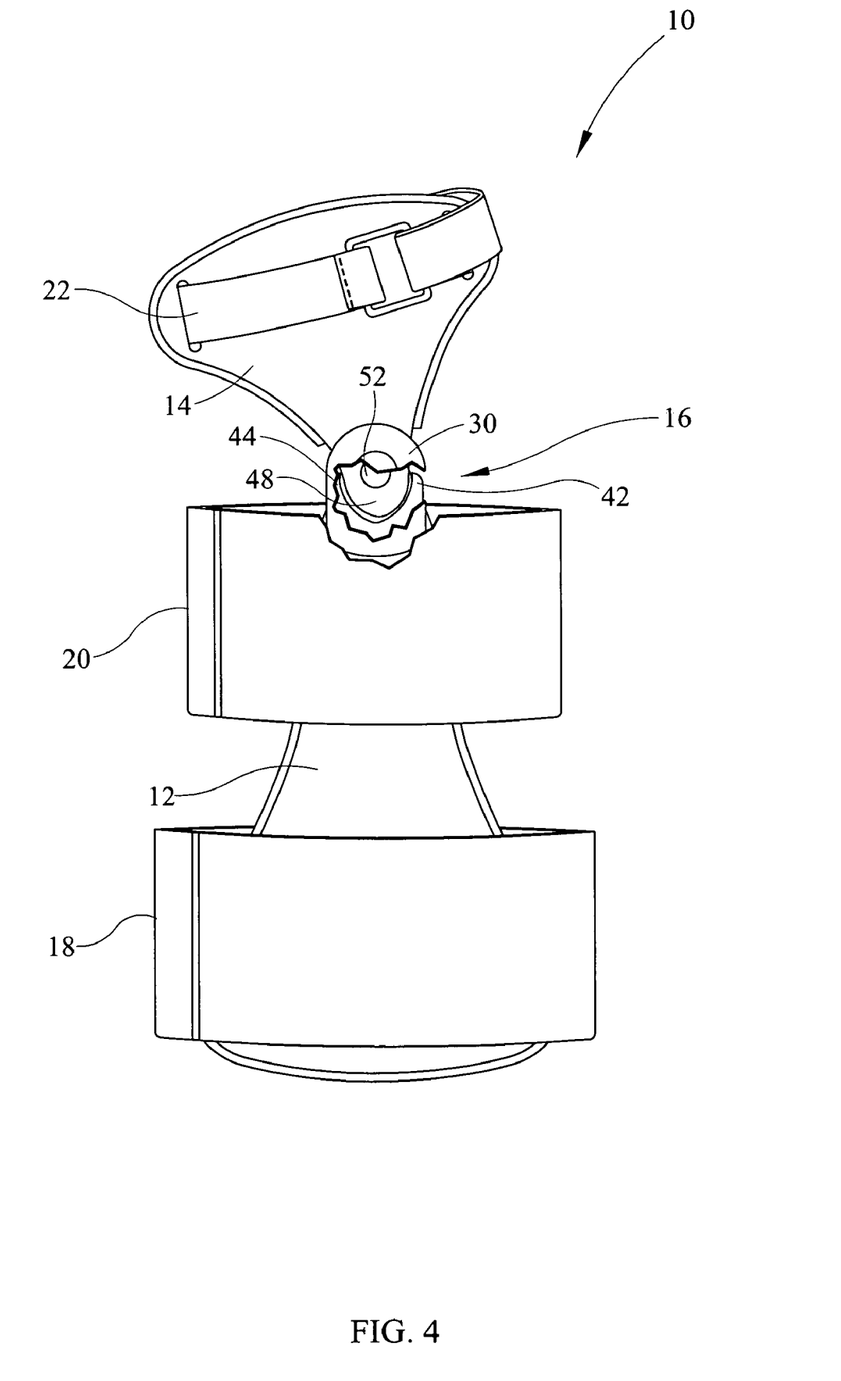
FIG. 4 is a top view of the brace of FIG. 1 disposed in a radial direction.
Figure 5:
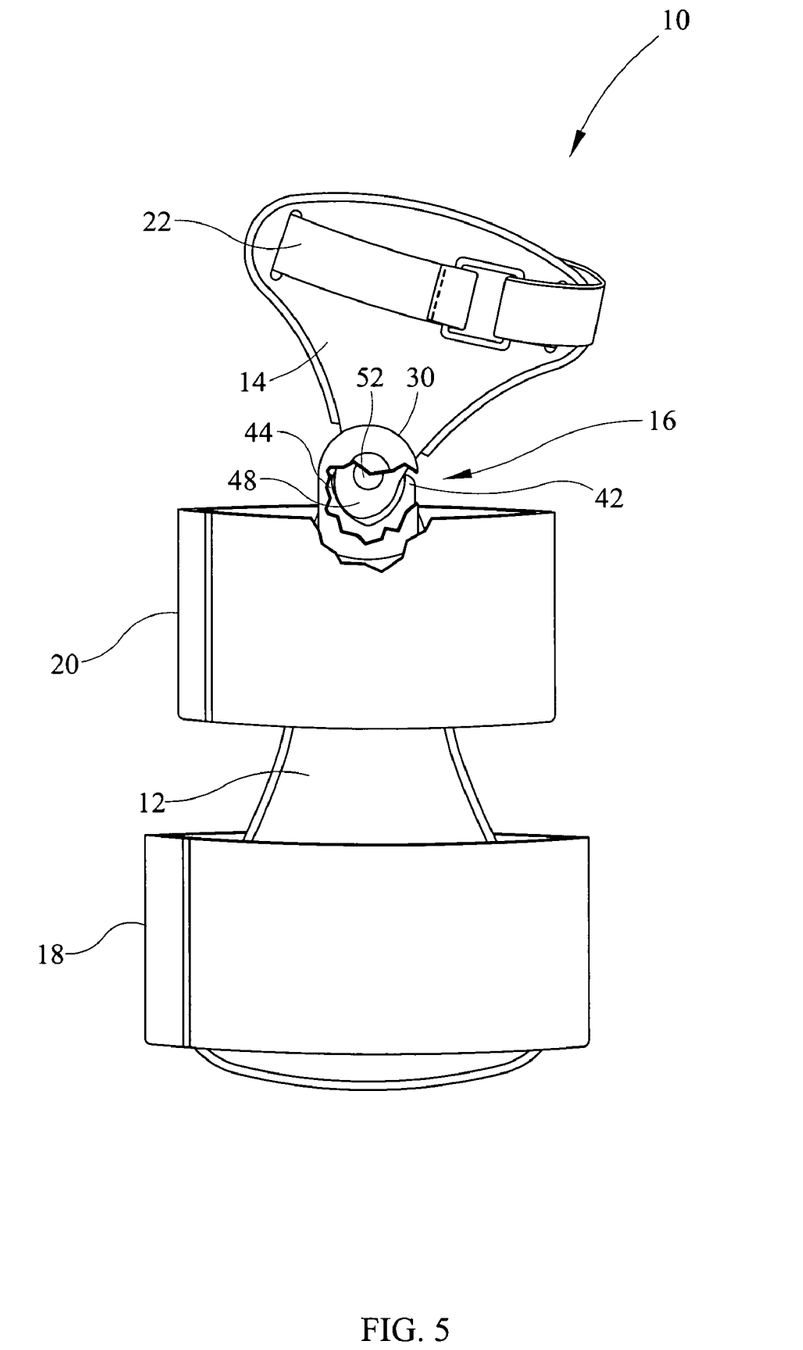
FIG. 5 is a top view of the brace of FIG. 1 disposed in an ulnar direction.

Referring now to FIG. 4, a top view of the hinged carpal tunnel splint 10 is depicted. The rigid second splint portion 14 is pivoted at hinge 16 in a radial direction toward the thumb, for example when worn on a patient's right hand and arm. The hinge 16 allows pivoting motion about a substantially vertical axis however the axis of rotation may be moved slightly from a vertical reference by heating and reforming the first and second splint portions 12, 14. Alternatively, referring to FIG. 5, the second splint portion 14 is pivoted at hinge 16 in an ulnar direction, for example if used on a patient's right hand and arm.

Figure 6:
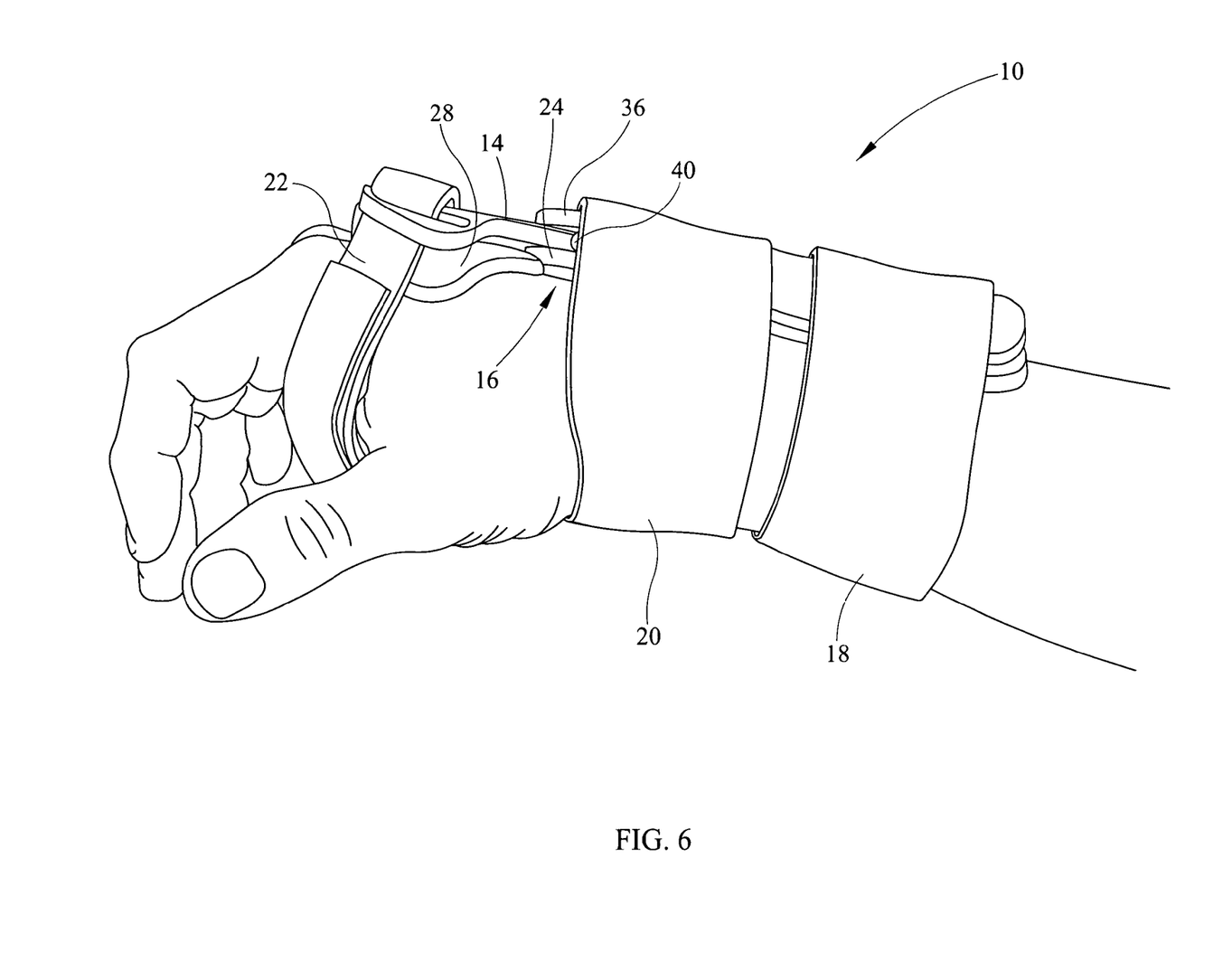
FIG. 6 is a side view of the brace of FIG. 1 positioned on a patient.

Referring now to FIG. 6, a side view of the hinged carpal tunnel brace 10 is depicted on a patient's right hand and arm. The upper arm strap 18 is wrapped around the patients forearm and the upper portion of the splint portion 12. The lower arm strap 20 wraps around the lower portion of the splint portion 12 adjacent the patient's wrist and the hinge 16. The hand strap 22 extends around the rigid second splint portion 14 and through the strap apertures 50 (FIG. 2). Moreover, the strap 22 captures the patient's fingers while allowing movement of the thumb and not further inhibiting motion thereof. Such design also allows the patient use of the palm, which prior art devices often fail to allow.

The hinge 16 shows the constructed hinge components including the upper washer 36, the rotation limiting spacer 40 and first and second splint portions 12, 14 which in combination define the hinge 16. Further, the upper padding 24 is depicted as being pressed against the user's wrist so that the rigid splint portions 12, 14 inhibit pivoting of the wrist about a horizontal axis or in flexion and extension directions. By limiting such flexion and extension pivoting, the median nerve is protected from compression by the tendons of the carpal tunnel. In other words, the patient's tendons can heal eliminating the symptoms of carpal tunnel syndrome.

Figure 7:
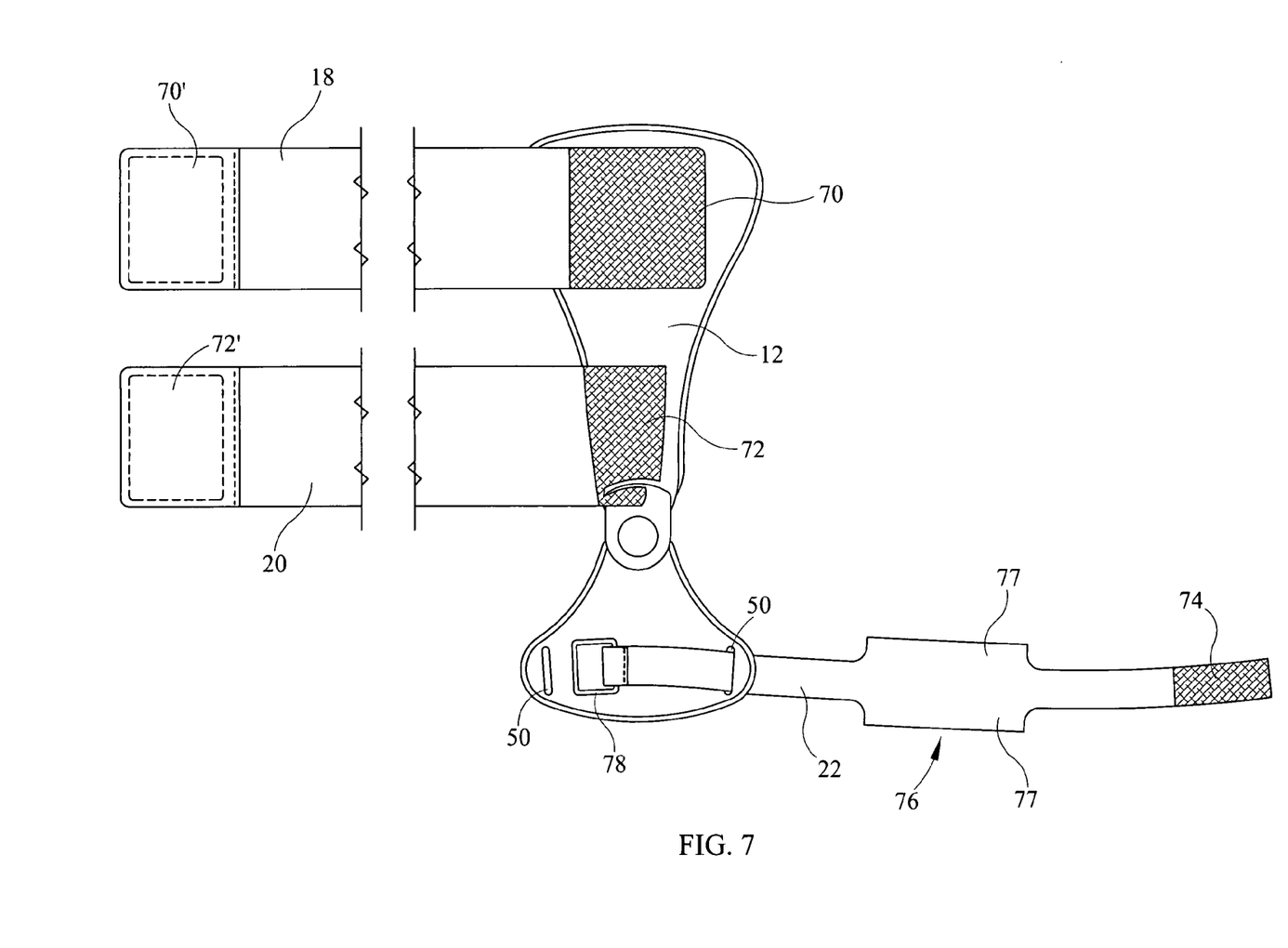
FIG. 7 is a top view of the brace of FIG. 1 depicting the straps in extended positions and the flaps defining the integral palm pad.

Referring now to FIG. 7, a top view of the hinged carpal tunnel splint 10 is depicted with the arm and hand straps 18, 20 and 22 depicted in fully extended positions. The arm upper straps 18,20 are made of a hook or loop fastening material. For example, upper strap 18 includes one of a hook and loop material along one side. At free end of the strap 18 the other of the hook or loop material is fastened to the material for engagement when wrapped around the patient's arm. The fastening areas of the strap 18 are indicated by cross-hatching so that one of the hook and loop material 70 is indicated on an upper surface of the strap 18 and the other of the hook and loop material 70' is disposed on the free end of the strap 18. Further, the lower strap 20 comprises one of the hook and loop material 72 along at least one side of the strap and the other of the hook and loop material 72' at the free end of the strap 20 for engagement therewith when the strap is wrapped around a patient's arm.

Figure 8:
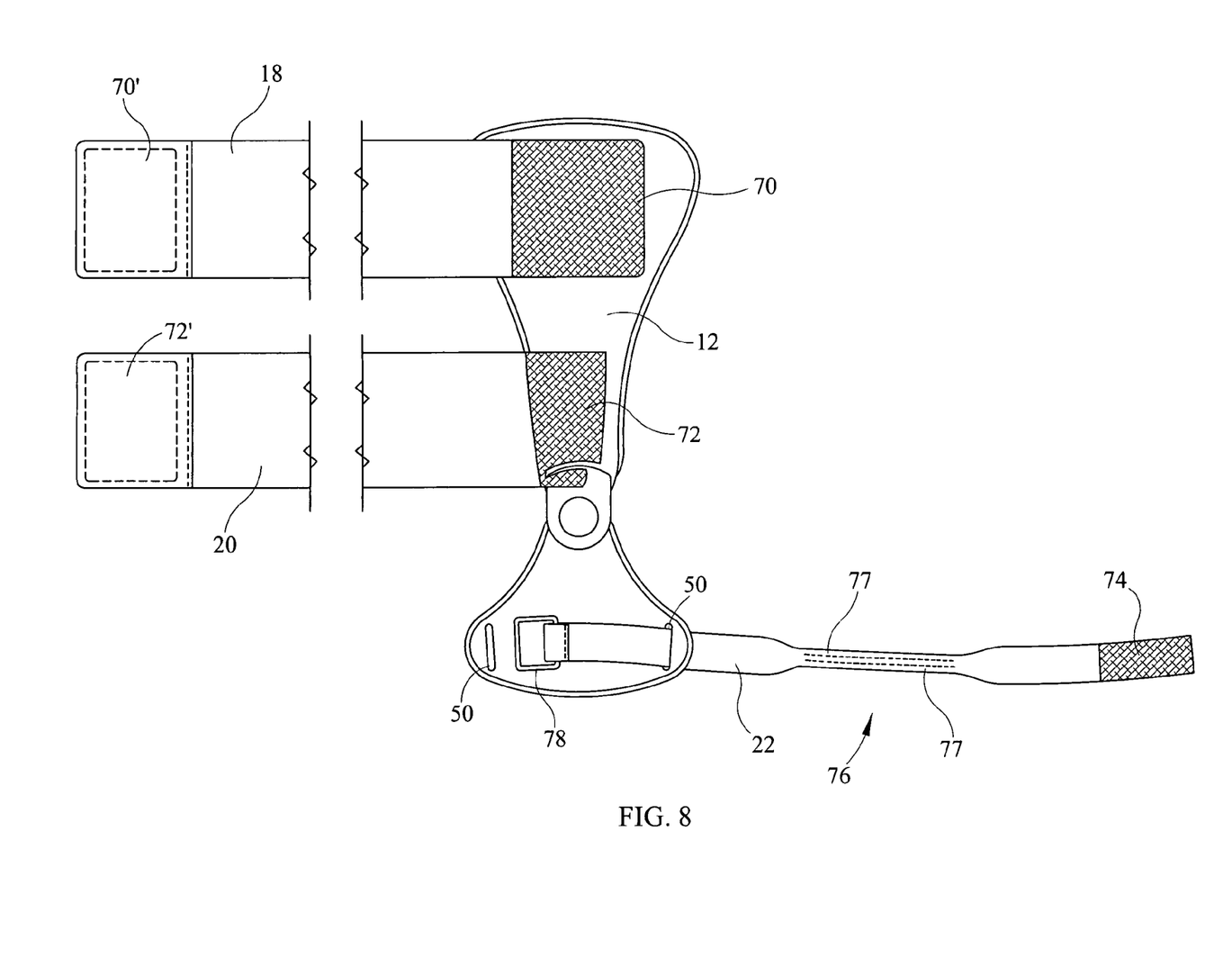
FIG. 8 is a top view of the brace with the straps in a fully extended position and the palm pad formed.

Referring now to FIGS. 7 and 8, the hand strap 22 also comprises one of a hook and loop material. The other of the hook and loop material is disposed at a free end of the strap 22. The hand strap 22 extends through the strap aperture 50 and is shown in an extended position prior to completion of manufacture. At one end of the strap is a buckle 78. The opposite end of the strap 22 is wrapped around a patient's fingers and extends upwardly through the opposite strap aperture 50 and re-engages the buckle 78. The end of the hand strap 22 has a hook material 74 which engages the loop surface of the hand strap 22 to fasten the hand strap 22 tightly around a patient's hand. As shown in FIG. 7, the hand strap 22 includes a palm pad 76 which is defined by integral flaps 77 on the hand strap 22. As shown in FIG. 7, the integral flaps are fully extended prior to completion of manufacture. Referring to FIG. 8, the palm pad 76 is formed by rolling or folding the integral flaps inwardly toward the center of the strap 22 and sewing them down to the surface of the palm pad 76 providing a thickened portion which engages a patient's palm and provides cushioning for the patient's hand.

Figure 10:
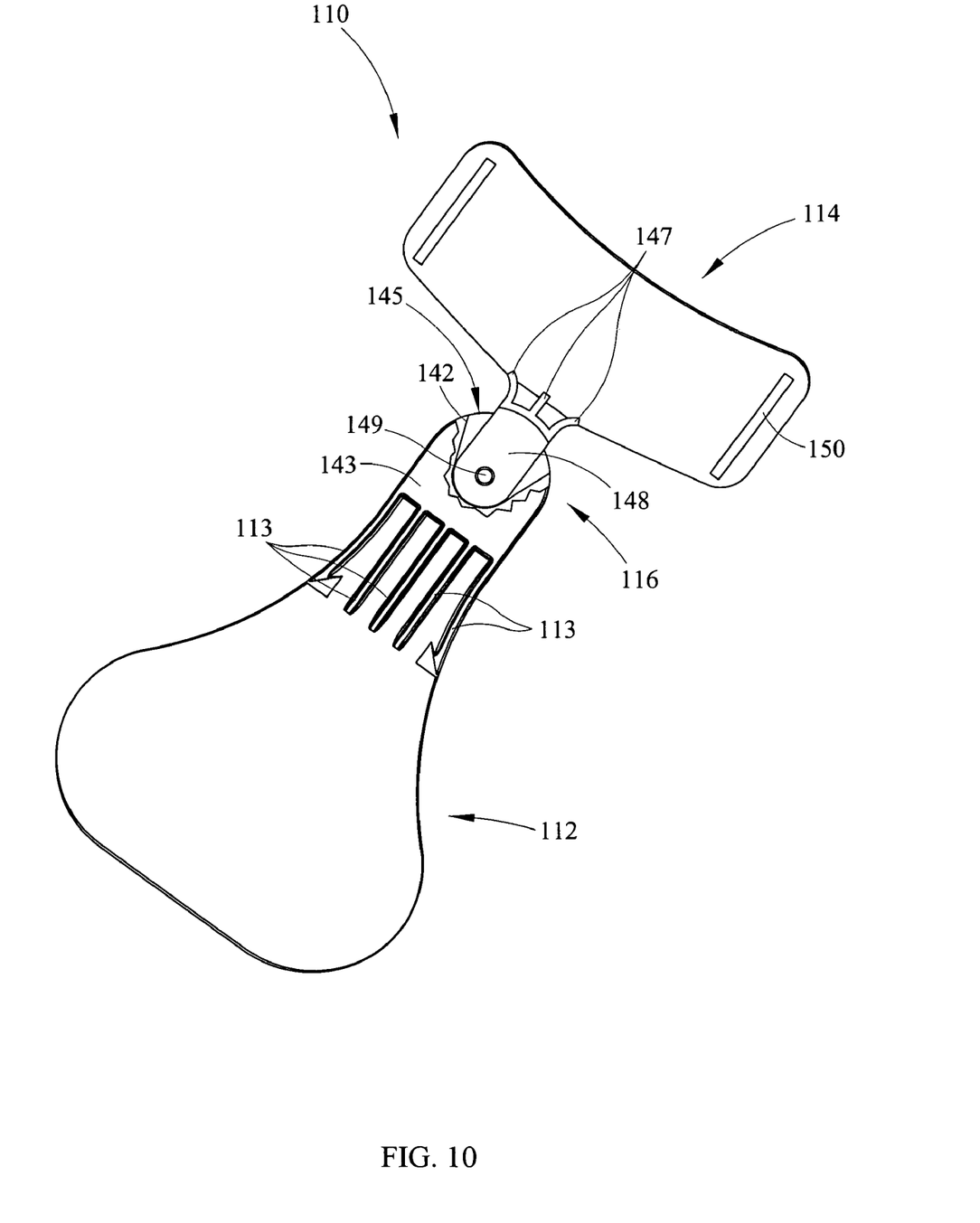
FIG. 10 is a top view of an alternative embodiment of the hinged dorsal carpal tunnel brace with a cut-away portion depicting the hinge area.
Figure 11:
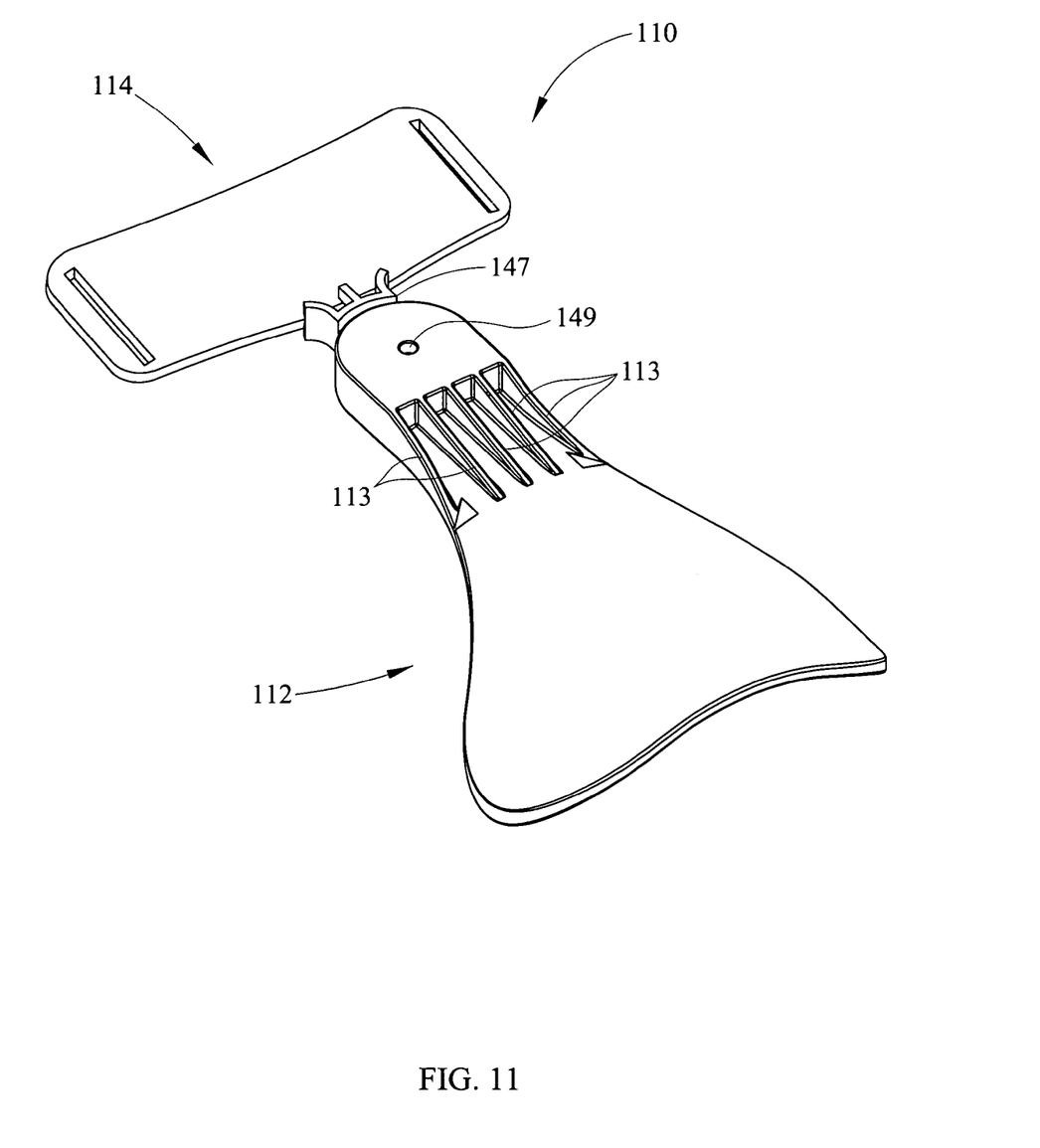
FIG. 11 is a upper perspective of the alternative embodiment of FIG. 10.
Figure 12:
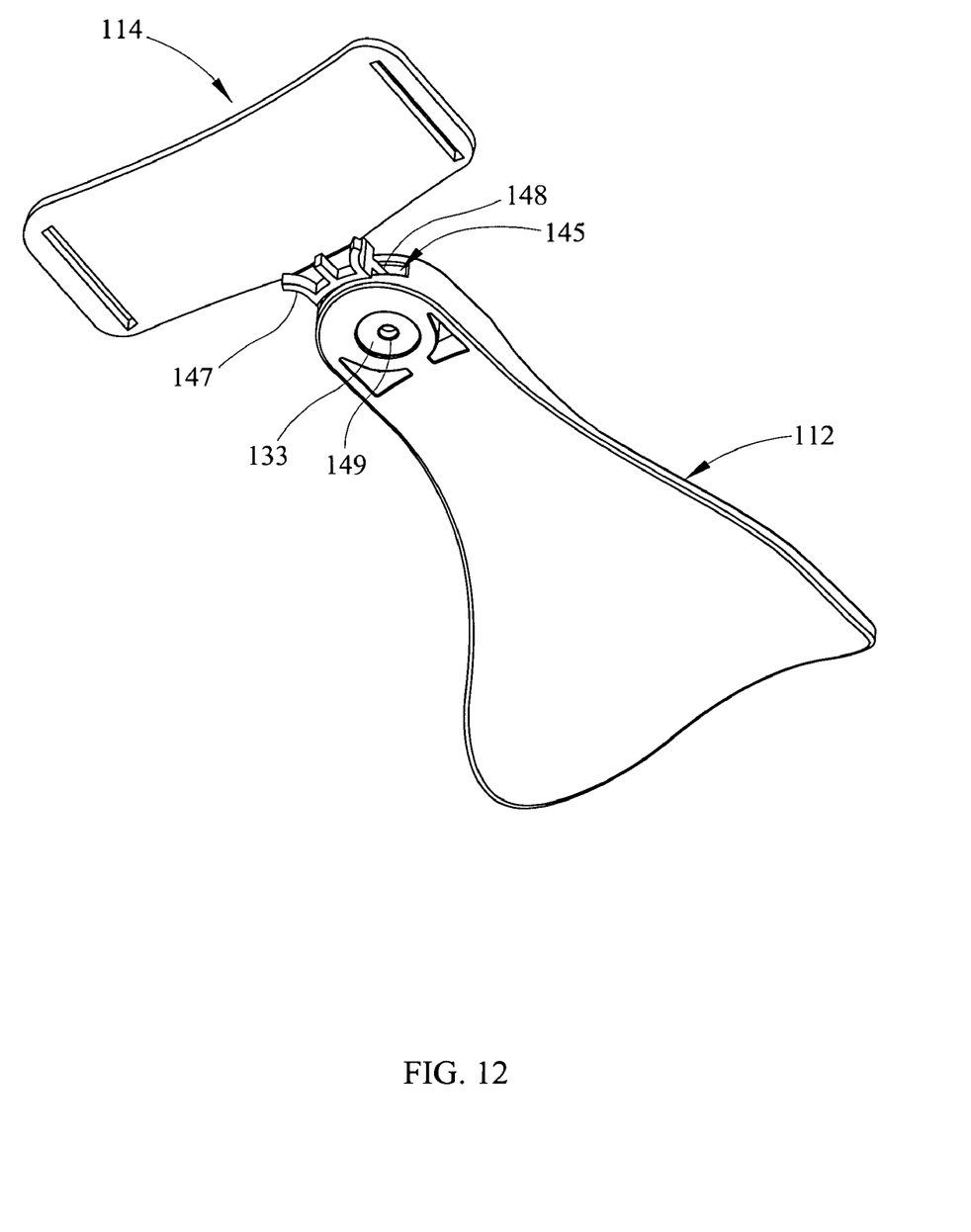
FIG. 12 is a lower perspective view of the alternative embodiment of FIG. 10

Referring now to FIGS. 10–12, an alternative embodiment of a hinged dorsal carpal tunnel brace 110 is shown comprising a first splint portion 112 and a second splint portion 114 hingedly attached at a hinge 116. The hinge 116 is an internal hinge covering the hinge components and protecting them from damage due to wear, dirt, and the like. The first splint portion 112 extends from near the patient's wrist and along a dorsal length of the forearm. The second splint portion 114 is positioned along the upper or dorsal surface of the patient's hand. The first splint portion 112 is elongate as previously described and includes a plurality of stiffening ribs 113 adjacent the hinge area 116. The stiffening ribs 113 taper from the upper surface of the first splint portion 112 to an upper hinge surface 143. The upper hinge surface 143 extends to an edge of the first splint portion 112 adjacent the second splint portion 114 and is also parallel to a lower surface of the first splint portion 112 thereby defining an opening 145 and an internal hinge area.

At one end of the first splint portion 112, the hinge 116 is defined within the opening 145. A tongue 148 extends from a pivotal connection within the opening 145 of the first splint portion 112 to provide pivotal motion for the second splint portion 114. The hinge 116 is defined by a fastener, the first splint portion 112, and the tongue 148.

The second splint portion 114 is substantially rectangular in shape and may be curved or slightly arcuate in order to be positioned along a dorsal surface of a user's hand. The second splint portion 114 comprises first and second strap apertures 150 which are utilized to attach a strap or loop as previously described. Extending from an upper edge of the second splint portion 114 adjacent the first splint portion 112 are a plurality of stiffeners 147 which extend from the second splint portion 114 to the tongue 148 and provide a rigid connection therebetween. The stiffeners 147 define a curved edge which extends along the adjacent edge of the first splint portion 112 at the hinge 116. The curved edge does not inhibit radial movement of the tongue 148 relative to the first splint portion 112. The stiffeners 147 also function to inhibit extension or flexion movement of the wrist when the patient is wearing the brace 110. In order words, the stiffeners 147 inhibit bending of the tongue 148 and bending at the connection of the tongue 148 and second splint portion 114. As shown in FIG. 10, the upper hinge surface 143 is cut-away to reveal the position of the tongue 148 within the opening 145 of the first splint portion 112. The tongue 148 comprises a fastening aperture 149 which is aligned with fastening apertures in the upper hinge surface 143 and the lower surface of the first splint portion 112. As depicted, the fastening aperture 149 is substantially vertically oriented providing for pivotal motion substantially about a vertical axis when a fastener is inserted. Within the opening 145 is a stop wall 142 which is curvilinear in shape and defines end points of opening 145. The end points of the stop wall 142 define the opening 145. The stop wall 142 functions as a rotation limiting device inhibiting rotation of the second splint portion 114 relative to the first splint portion 112 beyond a preselected range. In the exemplary embodiment the second splint portion 114 may rotate through 40 degrees, 20 degrees on either side of the centered position.

Referring now to FIG. 11, the hinged dorsal carpal tunnel brace 110 is shown from above in a perspective view. The curved rear edge of the stiffeners 147 is depicted adjacent the curved upper edge of the upper hinge surface 143 allowing movement of the stiffeners 147 and the integral second splint portion 114 relative to the first splint portion 112. Also depicted on the upper hinge surface 143 is a fastening aperture 149 extending through the upper hinge surface 143 and through the tongue 148.

Referring now to FIG. 12, a lower perspective view of the hinged dorsal carpal tunnel brace 110 is shown and depicts the connection between the second splint portion 114 and the first splint portion 112. The opening 145 is defined between the upper hinge surface 143 and the lower surface of the first splint portion 112. The opening 145 extends around the curved portion of the first splint portion 112 adjacent the second portion 114 through a pre-selected arcuate distance. In this exemplary embodiment the arc extends through about forty degrees, although this measurement may vary. Extending from the second splint portion 114 is a plurality of stiffeners 147 and a tongue 148 which is integrally connected to the second splint portion 114. The tongue 148 also extends from the second splint portion 114 into the first splint portion 112. Since the tongue 148 is pivotably attached within the opening of the first splint portion 112, the tongue 148 rotates through the opening 145 until the tongue 148 engages the stop wall 142 (FIG. 10). The hinge 116 is an internal hinge which is substantially surrounded by material to protect the hinge 116 from dirt or contact damage from wear. Further, the internal hinge design inhibits contact or pinching by the moving parts within the first splint portion 112.

As best seen in FIGS. 11 and 12, the stiffening ribs 113 have at least two functions. First the ribs 113 stiffen the narrow portion of the brace 110. Second the ribs 113 provide a height or thickness for the lower area of the first splint portion 112 wherein the opening 145 is defined and the tongue 148 may be positioned for pivotal movement. In other words, the ribs 113 form a thickened portion wherein a hinge area is defined. In this hinge area, the hinge is formed by the tongue 148 and first splint portion 112.

Also disposed along the lower surface of the first splint portion 112 is the aperture 149 through which a fastener may be positioned and a fastener recess 133 wherein a fastener head may be positioned. The fastener (not shown) extends vertically through the aperture 149 and may comprise a screw, a bolt, or a rivet which is positioned in the fastener recess 133 and extends through the first splint portion 112, the tongue 148 and the upper hinged surface 143 which hingedly connects the second splint portion 114 to the first splint portion 112.

As with the previously described embodiment, the alternative embodiment may utilize a plurality of straps for use on a patient. At least one strap may be positioned on the first splint portion 112. Further, at least one strap may be positioned on the second splint portion 114 through the strap apertures 150. The straps retain the brace 110 on the patient's arm and wrist allowing the first and second splint portions 112,114 to stabilize the carpal tunnel and reduce swelling. Also, as previously indicated, the hinged carpal tunnel brace 110 may comprise padding material along the lower surface of the first splint portion 112 and the second splint portion 114 to comfort the patient during use.

The foregoing description of several methods and an embodiment of the invention have been presented for purposes of illustration. It is not intended to be exhaustive or to limit the invention to the precise steps and/or forms disclosed, and obviously many modifications and variations are possible in light of the above teaching. It is intended that the scope of the invention be defined by the claims appended hereto.

What is claimed is:

1. A hinged dorsal carpal tunnel brace, comprising:
a first substantially arcuate dorsal splint portion for placement on a dorsal surface of a patient's forearm;
at least one strap for retaining said first arcuate dorsal splint portion on said patient's forearm;
a second dorsal splint portion for placement on a dorsal surface of a patient's hand;
at least one strap for fastening said second dorsal splint portion to said patient's hand;
a hinge pivotally connecting said first dorsal splint portion to said second dorsal splint portion and allowing pivotal motion through a preselected arcuate distance in radial and ulnar deviations while inhibiting flexion and extension;
a rotation limiting device limiting said pivotal motion to said preselected arcuate distance.

2. The hinged dorsal carpal tunnel brace of claim 1, said hinge disposed above a patient's wrist.

3. The hinged dorsal carpal tunnel brace of claim 1, said second dorsal splint portion comprising at least one strap aperture.

4. The hinged dorsal carpal tunnel brace of claim 1 further comprising a hand strap extending through at east one strap aperture of said second dorsal splint portion and defining a finger loop.

5. The hinged dorsal carpal tunnel brace of claim 4, said hand strap further comprising an integral palm pad.

6. The hinged dorsal carpal tunnel brace of claim 5 further comprising a lobe engaging said rotation limiter to limit rotation of said second dorsal splint portion relative to said first dorsal splint portion to a preselected arcuate distance.

7. The hinged dorsal carpal tunnel brace of claim 1 said rotation limiting device integrally formed with one of the first or second dorsal splint portions.

8. The hinged dorsal carpal tunnel brace of claim 1, said first splint dorsal portion having a pin aperture and said second splint dorsal portion having a pin aperture, said pin apertures being aligned.

9. The hinged dorsal carpal tunnel brace of claim 8 further comprising a fastener extending through said pin apertures and defining said hinge.

10. The hinged dorsal carpal tunnel brace of claim of claim 1, said first dorsal splint portion and said second dorsal splint portion each comprising a pad along a lower surface.

11. The hinged dorsal carpal tunnel brace of claim 1 said at least one strap disposed along the second dorsal splint portion being adjustable.

12. The hinged dorsal carpal tunnel brace of claim 1 said second dorsal splint portion being arcuate in cross-section.

13. A hinged dorsal carpal tunnel brace comprising:
a first brace portion pivotally connected to a second brace portion for rotation of said first portion relative to said second portion;
a hinge providing one degree of freedom and allowing radial and ulnar deviation of said second brace portion relative to said first brace portion through a preselected arcuate distance and inhibiting extension and flexion;
a first strap connected to said first brace portion and a second strap connected to said second brace portion, said second strap defining a finger loop and having an integral palm pad,
a rotation limiting spacer for space limiting rotation of said second brace portion relative to said first brace portion.

14. The hinged carpal tunnel brace of claim 13, said first brace and said second brace being formed of heat formable polymeric material.

15. A hinged dorsal carpal tunnel brace, comprising:
a first dorsal splint portion comprising a thickened portion;
a hinge area within said thickened portion;
said thickened portion having a stop wall limiting rotation within said hinge area;
a second dorsal splint portion pivotally connected to said first dorsal splint portion within said hinge area to allow limited radial and ulnar deviation while inhibiting flexion and extension;
said first and second dorsal splint portions each comprising at least one strap for retaining said brace on a patient.

16. The hinged dorsal carpal tunnel brace of claim 15 further comprising a plurality of stiffness extending from said second dorsal splint portion along a tongue toward said first dorsal splint portion.

17. The hinged dorsal carpal tunnel brace of claim 15 further comprising a tongue integral with said second splint portion, said tongue extending into an opening in said thickened portion of said first splint portion.

18. The hinged dorsal carpal tunnel brace of claim 17, said opening extending through an arcuate distance at said thickened portion of said first splint portion.

19. The hinged dorsal carpal tunnel brace of claim 15 further comprising a tongue extending from said second splint portion to said hinge area of said first splint portion and engaging said stop wall.

20. A hinged dorsal carpal tunnel brace, comprising:
a hand splint and an arm splint, said hand splint pivotally connected to said arm splint;
a thickened portion of said arm splint comprising an opening;
a tongue extending from said hand splint into said opening of said arm splint and defining said pivotal connection;
a stop wall in said thickened portion engaging said tongue at maximum movement positions;
said hand splint and said arm splint each comprising at least one strap for retaining said brace on a patient.

21. The hinged dorsal carpal tunnel brace of claim 20, said opening being arcuate.

22. The hinged dorsal carpal tunnel brace of claim 20, said brace allowing limited pivoting of said hand splint about a vertical axis trough a preselected angle.

* * * * *